US010407366B2

(12) United States Patent
Stochniol et al.

(10) Patent No.: US 10,407,366 B2
(45) Date of Patent: Sep. 10, 2019

(54) COMBINED PREPARATION OF BUTENE AND OCTENE FROM ETHENE

(71) Applicant: Evonik Degussa GmbH, Essen (DE)

(72) Inventors: Guido Stochniol, Haltern am See (DE); Helene Reeker, Dortmund (DE); Stephan Peitz, Oer-Erkenschwick (DE); Dietrich Maschmeyer, Recklinghausen (DE); Joerg Schallenberg, Dorsten (DE); Horst-Werner Zanthoff, Muelheim a.d. Ruhr (DE); Harald Haeger, Luedinghausen (DE)

(73) Assignee: Evonik Degussa GmbH, Essen (DE)

( * ) Notice: Subject to any disclaimer, the term of this patent is extended or adjusted under 35 U.S.C. 154(b) by 109 days.

(21) Appl. No.: 15/000,807

(22) Filed: Jan. 19, 2016

(65) Prior Publication Data

US 2016/0207848 A1   Jul. 21, 2016

(30) Foreign Application Priority Data

Jan. 19, 2015   (EP) .................................... 15151621

(51) Int. Cl.
| | | |
|---|---|---|
| C07C 2/24 | (2006.01) | |
| C07C 7/04 | (2006.01) | |
| C07C 2/10 | (2006.01) | |

(52) U.S. Cl.
CPC ................. *C07C 7/04* (2013.01); *C07C 2/10* (2013.01); *C07C 2521/12* (2013.01);
(Continued)

(58) Field of Classification Search
CPC .............................................. C07C 2/04–36
See application file for complete search history.

(56) References Cited

U.S. PATENT DOCUMENTS

| | | |
|---|---|---|
| 2,581,228 A | 1/1952 | Bailey et al. |
| 2006/0229480 A1* | 10/2006 | Blann ............ B01J 31/14 585/535 |

(Continued)

FOREIGN PATENT DOCUMENTS

| | | |
|---|---|---|
| CN | 103172485 A | 6/2013 |
| JP | 2003326169 A | 11/2003 |
| WO | WO 2014/154798 A1 | 10/2014 |

OTHER PUBLICATIONS

Ye et al. "A Tandem Catalytic System for the Synthesis of Ethylene-Hex-1-ene Copolymers from Ethylene Stock", Macromolecular Rapid Communications, 2004, 25, 647-652.*
(Continued)

*Primary Examiner* — In Suk C Bullock
*Assistant Examiner* — Ali Z Fadhel
(74) *Attorney, Agent, or Firm* — Grüneberg and Myers PLLC

(57) ABSTRACT

A process for the combined preparation of a butene and an octene from ethene, proceeds by: a) providing a solvent having a boiling point or boiling range above the boiling points of the butenes and below the boiling points of the octenes and wherein the solvent is an inert solvent or is hexene alone or is hexene admixed with pentane or hexane or heptane or is a mixture of pentane, hexane, and heptane; b) providing a first feed mixture containing at least the solvent and ethene dissolved therein; c) providing a second feed mixture containing at least hexene, the solvent and also ethene dissolved in the solvent and/or in the hexene; d) transferring the first feed mixture into a first synthesis and the second feed mixture into a second synthesis, wherein the first and second syntheses are physically separated from one another; e) oligomerizing of at least part of the ethene present in the first feed mixture in the presence of a first heterogeneous catalyst and in the presence of the solvent in
(Continued)

the first synthesis to give a first reaction mixture comprising at least the solvent, butene and hexene; f) separating a butene-containing low boiler fraction from the first reaction mixture or from a stream based on the first reaction mixture; g) separating an intermediate boiler fraction containing hexene and the solvent from the first reaction mixture or from a stream based on the first reaction mixture; h) using at least part of the intermediate boiler fraction in the course of providing the second feed mixture; and i) reacting at least part of the ethene present in the second feed mixture with at least part of the hexene present in the second feed mixture in the presence of a second heterogeneous catalyst and in the presence of the solvent in the second synthesis to give a second reaction mixture comprising at least octene and the solvent.

13 Claims, 4 Drawing Sheets

(52) U.S. Cl.
    CPC ......... *C07C 2523/755* (2013.01); *Y02P 20/52* (2015.11); *Y02P 20/582* (2015.11)

(56) References Cited

U.S. PATENT DOCUMENTS

| | | | |
|---|---|---|---|
| 2007/0185362 A1* | 8/2007 | Lattner | C07C 2/32 585/521 |
| 2007/0191661 A1* | 8/2007 | Brown | C07C 2/12 585/517 |
| 2009/0312583 A1* | 12/2009 | Sigl | C07C 2/12 568/909 |
| 2011/0288256 A1 | 11/2011 | Vermeiren | |
| 2011/0306812 A1* | 12/2011 | Rohde | C07C 2/12 585/326 |
| 2012/0016097 A1* | 1/2012 | Weber | C07C 2/30 526/348 |
| 2013/0158321 A1 | 6/2013 | Olivier-Bourbigou et al. | |
| 2014/0012059 A1* | 1/2014 | Vinel | C07C 7/04 585/809 |

OTHER PUBLICATIONS

Singaporean Written Opinion dated May 20, 2016 in Patent Application No. 10201600375R filed Jan. 18, 2016.
Combined Taiwanese Office Action and Search Report completed on Dec. 29, 2016 in Patent Application No. 105101236 (submitting English translation only).

* cited by examiner

COMBINED PREPARATION OF BUTENE AND OCTENE FROM ETHENE

BACKGROUND OF THE INVENTION

Field of the Invention

The invention is concerned with the combined preparation of butene and octene from ethene.

Discussion of the Background

Hydrocarbons are chemical compounds which consist exclusively of carbon and hydrogen. Alkenes (synonym: Olefins) are hydrocarbons which have a C=C double bond in the molecule. Alkanes (synonym: Paraffins), on the other hand, are hydrocarbons which have only single bonds. They are therefore also referred to as saturated.

In organic chemistry, hydrocarbons are frequently designated according to the number of carbon atoms which they have per molecule, by the respective class of substances being preceded by the prefix $C_n$. Here, n is the respective number of carbon atoms in a molecule. Thus, $C_4$-olefins are substances from the class of alkenes having four carbon atoms. $C_8$-olefins correspondingly have eight carbon atoms per molecule. Where the prefix $C_{n+}$ is used in the following, it refers to a class of substances which have more than n carbon atoms per molecule. A $C_{4+}$-olefin accordingly has at least five carbon atoms.

The simplest olefin is ethene (ethylene). It has two carbon atoms. Ethene is an important basic chemical and is therefore prepared in large quantities. This is usually effected by steam cracking of naphtha. In addition, it can be obtained by dehydrogenation of ethane, which in turn is a constituent of natural gas. Owing to the increasing exploitation of unconventional sources of natural gas and decreasing recovery of petroleum, the proportion of ethene based on natural gas is steadily increasing.

$C_4$-olefins encompass the four isomeric materials 1-butene, cis-2-butene, trans-2-butene and isobutene. 1-Butene and the two 2-butenes belong to the group of the linear butenes, while isobutene is a branched olefin. The linear $C_4$-olefins 1-butene, cis-2-butene and trans-2-butene are often summarised as "n-butene" in the literature. Depending on the thermodynamic circumstances, the four isomeric $C_4$-olefins usually occur together. For this reason, no distinction is made between singular and plural when the term "butene" is used. When reference is made here to "butene" with no further details being specified, what is meant is a linear alkene having four carbon atoms (or n-butene) or a mixture containing different isomeric alkenes having four carbon atoms.

A current overview of the chemical and physical properties of butenes and also the industrial processing and utilisation thereof is given by:

F. Geilen, G. Stochniol, S. Peitz and E. Schulte-Koerne: Butenes. Ullmann's Encyclopedia of Industrial Chemistry. (2013)

Butenes are nowadays predominantly obtained in the cracking of petroleum fractions in a steam cracker or in a fluid catalytic cracker (FCC) and are used as intermediate for the preparation of a variety of industrial chemicals.

In the following, a "hexene" is an olefin having six carbon atoms or a mixture containing a plurality of different $C_6$-olefins. For this reason, no distinction is made between singular and plural when using the term "hexene". The $C_6$-olefins include the eighteen isomers 1-hexene, (E)-2-hexene, (Z)-2-hexene, (E)-3-hexene, (Z)-3-hexene, 2-methyl-1-pentene, 2-methyl-2-pentene, (R)-3-methyl-1-pentene, (S)-3-methyl-1-pentene, (E)-3-methyl-2-pentene, (Z)-3-methyl-2-pentene, 4-methyl-1-pentene, (E)-4-methyl-2-pentene, (Z)-4-methyl-2-pentene, (3S)-2,3-dimethyl-1-butene, (3R)-2,3-dimethyl-1-butene, 2,3-dimethyl-2-butene and 3,3-dimethyl-1-butene.

However, only the substances 1-hexene and 4-methyl-1-pentene, which are used as monomers or comonomers in the production of plastics, are of industrial interest. For this purpose, they are prepared from ethene or from the $C_3$-olefin propene by oligomerisation. The oligomerisation will be explained in detail below.

For the purposes of the present invention, octene is an olefin having eight carbon atoms or a mixture containing a plurality of different $C_8$-olefins. The $C_8$-olefins include a large number of isomers which are too many to list here. An industrially important representative of the $C_8$-olefins is 1-octene which is prepared by oligomerisation of ethene and is used as comonomer in polyethylene.

An alternative way of preparing octene is dimerisation of n-butene. The mixture of olefins having eight carbon atoms which is formed here is referred to as dibutene, and is thus a particular octene within the meaning of the terminology employed here. Dibutene is distinguished by the isomer distribution, in terms of which it differs from other octene mixtures.

Depending on the way in which the individual n-butene molecules are joined in the course of the oligomerisation, an oligomer having a different degree of branching is obtained. The degree of branching is described by the iso index, which states the mean number of methyl groups per $C_8$ molecule in the isomer mixture. The iso index for dibutene is defined as follows:

$$\text{Iso index} = (\text{proportion by weight of methylheptenes} + 2 * \text{proportion by weight of dimethylhexenes})/100$$

Thus, n-octenes contribute 0, methylheptenes contribute 1 and dimethylhexenes contribute 2 to the iso index of a product mixture of $C_8$-olefins. The lower the iso index, the less branched are the molecules in the mixture.

A low degree of branching is always important when the olefin mixture is to be used as starting material for preparing plasticizers. Scientific studies demonstrate that the degree of branching of olefin mixtures which are processed further by hydroformylation, hydrogenation and esterification to give plasticizers is critical to the properties and quality of the plasticizer.

The iso index which a $C_8$-olefin mixture has to achieve in order to be able to serve as starting material for high-quality plasticizers depends on the respective requirements of the plasticizer customers and changes over time. At present, an iso index of less than 1.1 is usually required.

For the purposes of the present invention the oligomerisation which has now been mentioned a number of times is the reaction of hydrocarbons with themselves, forming corresponding longer-chain hydrocarbons. Olefins having from two to eight carbon atoms can be oligomerised very readily.

Thus, for example, an olefin having six carbon atoms (hexene) can be formed by oligomerisation of two olefins having three carbon atoms. The oligomerisation of two molecules with one another is also referred to as dimerisation. If, in contrast, three olefins having three carbon atoms are joined to one another (trimerisation), the result is an olefin having nine carbon atoms. If n-butenes are subjected to an oligomerisation, essentially olefins having eight carbon atoms (more precisely: dibutene) and also olefins having twelve carbon atoms ($C_{12}$-olefins, "tributene") and to a lesser extent olefins having more than twelve carbon atoms ($C_{12}$+-olefins) are formed.

One process employed in industry for preparing dibutene by oligomerisation of n-butene is the Octol® process. Detailed description thereof can be found in the nonpatent literature, for example in:

B. Scholz: The HÜLS Octol Process: Heterogeneously catalysed dimerisation of n-butenes and other olefins. DGMK conference in Karlsruhe, published in Erdöl, Erdgas, Kohle, April 1989, pages 21 and 22.

R. H. Friedlander, D. J. Ward, F. Obenaus, F. Nierlich, J. Neumeister: Make plasticizer olefins via n-butene dimerisation. Hydrocarbon Processing, February 1986, pages 31 to 33.

F. Nierlich: Oligomerise for better gasoline. Hydrocarbon Processing, February 1992, pages 45 to 46.

In the patent literature, an oligomerisation based on the Octol® process is described, for example, in DE102008007081A1. EP1029839A1 is concerned with the fractionation of the $C_8$-olefins formed in the Octol® process.

The completely heterogeneously catalysed Octol® process gives a dibutene which has a low degree of branching and is highly suitable for the preparation of plasticizers. Heterogeneously catalysed means that the catalyst is present as a solid in the liquid or gaseous reaction mixture. The fluid reactants thus flow around the catalyst and the catalyst remains in the reactor.

The term cooligomerisation refers to the simultaneous oligomerisation of a plurality of substrates in one reaction vessel. Thus, EP2582648B1 describes the cooligomerisation of butene and octene to give dodecene ($C_{12}$-olefin). As in the case of any oligomerisation, which olefin reacts with which is not precisely known in a cooligomerisation: In the example of EP2582648B1, a dodecene can be formed both from three butenes and also from a butene and an octene. From a chemical point of view, any oligomerisation can be considered to be a cooligomerisation. From an industrial point of view, on the other hand, a cooligomerisation is present only when at least two olefins having different numbers of carbon atoms are introduced into a common reactor. In the choice of terminology, it is thus the controllable introduction of the starter materials which matters, not the reaction which actually takes place.

WO2005/123884 discloses the combined preparation of 1-octene and 1-hexene by tetramerisation and trimerisation of ethylene. For this purpose, two different homogeneous catalysts, namely a first catalyst for tetramerisation and a second catalyst for trimerisation, are provided in a common reaction vessel. Since the homogeneous catalysts used are dissolved in the reaction mixture, they have to be either recycled with retention of their catalytic activity by suitable methods or be completely separated off. Recycling of a homogeneous catalyst is associated with complicated engineering and considerable costs in terms of apparatus, which appears to be feasible only in the case of very expensive catalysts. The complete separation of a homogeneous oligomerisation catalyst from a reaction mixture is usually effected by quenching with water or alkaline, aqueous solutions. This leads to significant generation of aqueous, often chromium-containing salt solutions which have to be disposed of appropriately. In addition, the use of fresh catalyst solutions for the oligomerisation incurs relatively high costs.

Furthermore, this process also does not appear to be suitable for preparing $C_8$-olefins for use as starting material for plasticizers: Although up to 52% by weight of $C_8$-olefins are obtained in combined tetramerisation and trimerisation, the degree of branching is not specified precisely. Moreover, the process is optimised for the production of the comonomer 1-octene, viz. a $C_8$-olefin which in any case is not very suitable for plasticizer production. It is therefore not possible to see that the $C_8$-alkenes achieve an iso index which qualifies them as starting material for plasticizer production. In addition, the homogeneously dissolved catalyst would definitely have to be separated off in this use since the subsequent hydroformylation is likewise homogeneously catalysed and is sensitive to interference caused by extraneous catalysts introduced by entrainment.

What has just been said also applies to the process disclosed in WO2005/123633 for the oligomerisation of ethylene, which is carried out in the presence of cyclohexane. The cyclohexane serves as solvent and is intended to reduce the deactivation of the homogeneous catalyst used or its activator.

A similar situation also applies to US2013/0066128 A1 which is concerned with the homogeneous oligomerisation of ethene in n-heptane.

The problem of separating off the catalyst does not arise in heterogeneously catalysed processes in which the catalyst is present as a solid and remains in the reactor. Ethylene oligomerisation over a solid Si/Al/Ni system is described in U.S. Pat. No. 8,637,722B2. However, this process takes place in the gas phase, which is disadvantageous in terms of the utilisation of space by the reactors. In addition, the established process steps of further processing of butenes and octenes take place in the liquid phase, so that this gas-phase process is not readily compatible with existing technology. A need to liquefy the butenes and octenes obtained in the gas phase requires additional energy.

The gas-phase process disclosed in WO2010/117539A1 for oligomerisation of ethylene diluted in an FCC gas over a zeolitic Ni catalyst also cannot be readily incorporated into an established production train for C4/C8 utilisation.

A mixed form of heterogeneous and homogeneous oligomerisation is disclosed in US2013/0158321A1. Here, ethene is firstly dimerised homogeneously to form butenes and these are subsequently converted into octenes by heterogeneous catalysis over a solid nickel catalyst. Both reaction stages take place in the liquid phase in the presence of hexane. The reaction output from the first stage has to be neutralised by means of base and freed of the homogeneous catalyst (triethylaluminium) by distillation. This is very complicated in industrial practice.

SUMMARY OF THE INVENTION

It was an object of the present invention to provide a process for the combined preparation of at least butene and octene from ethene.

In the light of the related art, it was another object of the present invention to provide a process for the combined preparation of butene and octene from ethene, which gives primarily $C_8$-olefins having high linearity (i.e. a small degree of branching, low iso index). In addition, the process should give a high yield of 1-butene since this sought-after isomer can be marketed separately. It should be completely heterogeneously catalysed so that it is not necessary to operate a complicated catalyst removal in order to avoid contamination of downstream, homogeneously catalysed processes. Finally, the process should preferably be able to be carried out in the liquid phase in order to be compatible with established technologies for utilisation of butene and octene.

These and other objects are achieved by simultaneously carrying out two reactions, namely a first synthesis which primarily converts $C_2$ into $C_4$ and a second synthesis which converts $C_2$ and $C_6$ into $C_8$. The two reactions are carried out physically separately from one another and accordingly in different reactors or at least in different, physically separate regions of a reactor.

The present invention relates to a process for the combined preparation of a butene and an octene from ethene, said process comprising:

a) providing a solvent having a boiling point or boiling range above the boiling points of the butenes and below the boiling points of the octenes and wherein the solvent is an inert solvent or is hexene alone or is hexene admixed with pentane or hexane or heptane or is a mixture of pentane, hexane, and heptane;

b) providing a first feed mixture containing at least the solvent and ethene dissolved therein;

c) providing a second feed mixture containing at least hexene, the solvent and also ethene dissolved in the solvent and/or in the hexene;

d) transferring the first feed mixture into a first synthesis and the second feed mixture into a second synthesis, wherein the first and second syntheses are physically separated from one another;

e) oligomerising of at least part of the ethene present in the first feed mixture in the presence of a first heterogeneous catalyst and in the presence of the solvent in the first synthesis to give a first reaction mixture comprising at least the solvent, butene and hexene;

f) separating a butene-containing low boiler fraction from the first reaction mixture or from a stream based on the first reaction mixture;

g) separating an intermediate boiler fraction containing hexene and the solvent from the first reaction mixture or from a stream based on the first reaction mixture;

h) using at least part of the intermediate boiler fraction in the course of providing the second feed mixture; and i) reacting at least part of the ethene present in the second feed mixture with at least part of the hexene present in the second feed mixture in the presence of a second heterogeneous catalyst and in the presence of the solvent in the second synthesis to give a second reaction mixture comprising at least octene and the solvent.

Figure 1:
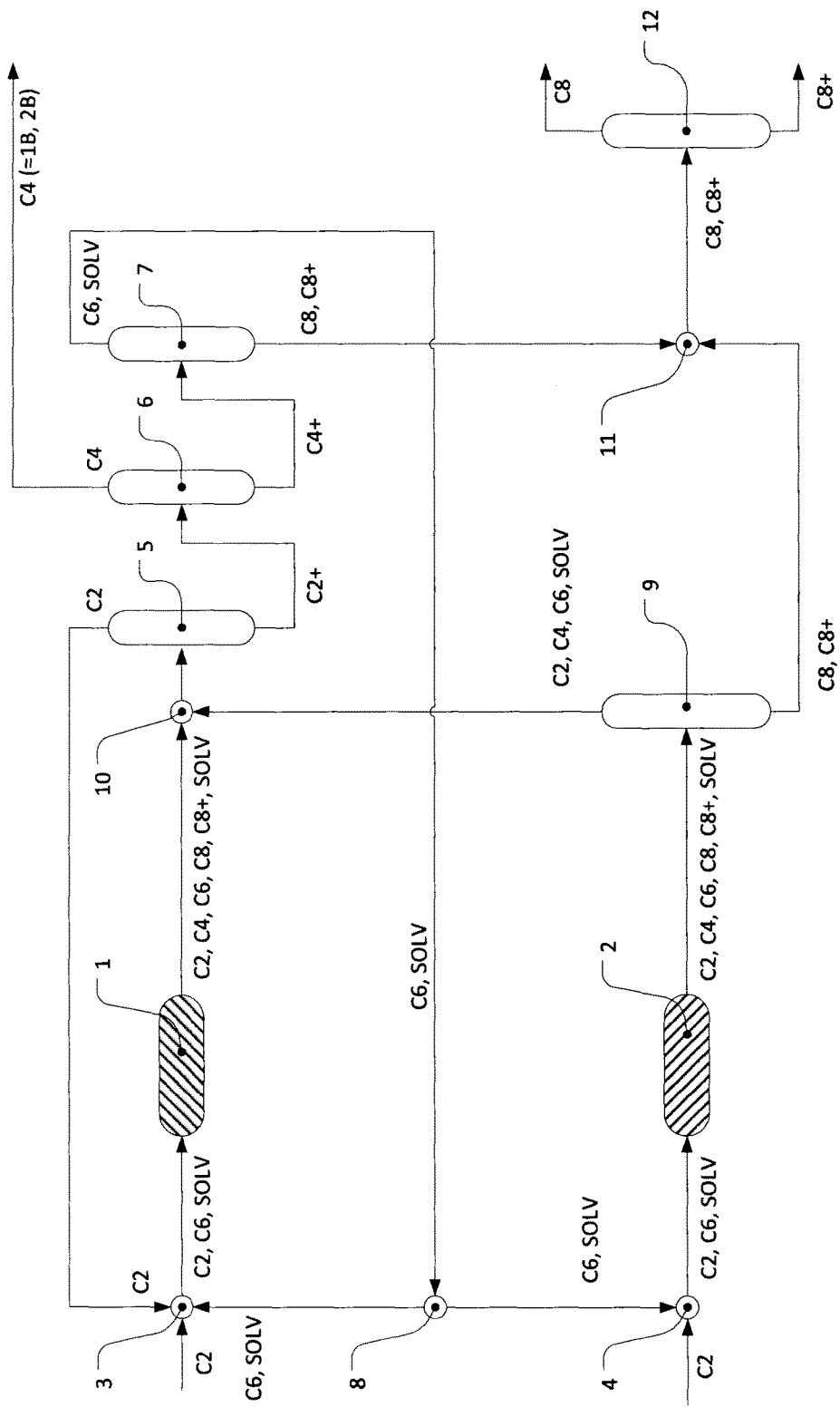
FIG. 1 shows a flow diagram for the basic process.

LIST OF REFERENCE SYMBOLS 1 first synthesis
2 second synthesis
3 first mixer
4 second mixer
5 first column
6 second column
7 third column
8 divider
9 fourth column
10 third mixer
11 fourth mixer
12 fifth column
13 sixth column
14 isomerisation
15 oxidative dehydrogenation
16 third synthesis
17 sixth mixer
C2 ethene
C4 butene (low boiler fraction, top of the second column)
C6 hexene
C8 octene
C8+ higher olefins
C2, C6, SOLV first or second feed mixture
C2, C4, C6, C8, C8+, SOLV first or second reaction output
C2+ bottoms from the first column
C4+ bottoms from the second column
C6, SOLV intermediate boiler fraction or overhead stream from the third column
C8, C8+ high boiler fraction or bottoms from the third column
C2, C4, C6, SOLV low and intermediate boiler fraction
1B 1-butene
2B 2-butene (cis and trans)
1B, 2B isomer mixture
BD butadiene
C4, C8, C12, C12+ third reaction mixture
SOLV solvent (hexane)

DETAILED DESCRIPTION OF THE INVENTION

A particular embodiment of the invention is constituted by the fact that both syntheses are carried out in the presence of an inert solvent. The selectivity of the reactions in the direction of butene or of octene can be influenced by means of the solvent. In the second synthesis in particular, the reaction of $C_2+C_6$ can be promoted relative to the reaction of $C_2+C_2$ by targeted setting of the concentration of ethene in the solvent or the hexene.

The inert solvent used has to satisfy two prerequisites:

Firstly, it has to be inert. This means that it does not undergo any chemical reactions under the conditions prevailing in the process (pressure/temperature in the reactions and columns). In particular, it should not react with ethene. The solvent is thus not consumed in the process. Naturally, it is not ruled out that the solvent will react in some form somewhere. However, these reactions should proceed so slowly compared to the desired reactions that they are not significant. The slow reaction may at most be noticeable as ageing of the solvent.

Secondly, the solvent should have a boiling point which is between the boiling points of the butenes and those of the octenes. It should thus have a boiling point higher than that of the highest-boiling butene in the process; but lower than that of the octene present in the process which has the lowest boiling point. If the solvent does not have a singular boiling point but instead has a boiling range (for instance because the solvent is a mixture and not a pure substance), the boiling range of the solvent should lie between the boiling point of the butenes and that of the octenes. The boiling points compared here are boiling temperatures at the same pressures.

A solvent which meets both prerequisites (boiling point position, inert behaviour) is, for example, the $C_6$-alkane n-hexane.

The advantage of using a solvent having this boiling point position is that it can be separated off easily via the bottom of the butene column, while a lower-boiling solvent, for instance, would need to be separated off at the top, which is associated with a greater energy consumption. Part of the solvent is ultimately formed by the hexene which is formed as by-product in the process and therefore does not have to be procured specially. Since the boiling position of the solvent corresponds essentially to that of the by-product hexene, the by-product can be separated off together with the solvent as intermediate boiler from the first reaction mixture and transferred to the second reaction.

However, the use of the inert solvent does not prevent hexene, octene and higher oligomers from being formed in addition to the desired butene in the first synthesis.

The process of the invention is additionally distinguished by the hexene formed by $C_2$ trimerisation in the first synthesis being used as starter material for the second synthesis. There, it is reacted with ethene to form octene, the second target product. The by-product of the first synthesis which is actually undesirable (hexene) is thus used further to form the target product octene. In addition, hexene is continually circulated and utilised as solvent for ethene. This makes it possible for both syntheses to be carried out in the liquid phase and be heterogeneously catalysed. These are further important aspects of the production process presented here.

DETAILED DESCRIPTION OF THE INVENTION

Specifically, the invention provides a process for the combined preparation of butene and octene from ethene, which comprises the steps a) to i):

a) provision of a solvent whose boiling point or boiling range is above the boiling points of the butenes and below the boiling points of the octenes; and which solvent is an inert solvent or is hexene alone or is hexene admixed with pentane or hexane or heptane or is a mixture of pentane, hexane, heptane;

b) provision of a first feed mixture containing at least the solvent and ethene dissolved therein;

c) provision of a second feed mixture containing at least hexene, the solvent and also ethene dissolved in the solvent and/or in the hexene;

d) transfer of the first feed mixture into a first synthesis and of the second feed mixture into a second synthesis, where the first and second syntheses are physically separate from one another;

e) oligomerisation of at least part of the ethene present in the first feed mixture in the presence of a first heterogeneous catalyst and in the presence of the solvent in the first synthesis to give a first reaction mixture comprising at least the solvent, butene and hexene;

f) separation of a butene-containing low boiler fraction from the first reaction mixture or from a stream based on the first reaction mixture;

g) separation of an intermediate boiler fraction containing hexene and the solvent from the first reaction mixture or from a stream based on the first reaction mixture;

h) use of at least part of the intermediate boiler fraction in the course of the provision of the second feed mixture;

i) reaction of at least part of the ethene present in the second feed mixture with at least part of the hexene present in the second feed mixture in the presence of a second heterogeneous catalyst and in the presence of the solvent in the second synthesis to give a second reaction mixture comprising at least octene and the solvent.

Since ethene is very reactive, it can be reacted completely in the first and second syntheses. However, it is advisable to stop the first reaction and/or the second reaction before complete conversion of the ethene so that unconsumed ethene remains in the first reaction mixture or in the second reaction mixture. The unconsumed ethene should be separated off from the respective reaction mixture and be reused for provision of the first and/or second feed mixture.

The background reason for not reacting the ethene completely is that the catalyst rapidly starts to isomerise the 1-alkenes as soon as the ethene has been consumed to a particular extent. The isomerisation partly occurs even beforehand, but the butenes formed from ethene then compete with the ethene for the catalytically active sites. Stopping the reaction before complete consumption of the ethene thus results in a higher 1-butene content.

According to the invention, the first synthesis is optimised for the production of 1-butene. In addition, $C_2$ is unavoidably dimerised to $C_4$ in the second synthesis intended for the production of octene. It is advisable to work up the butene which is formed as by-product in the second synthesis and is thus present in the second reaction mixture together with the butene present in the first reaction mixture. Distillation columns can be saved as a result of this measure. Although the columns utilised jointly have to be made larger, which increases the capital costs, operation of these is then more advantageous since maintenance and energy costs are lowered.

The butene present in the first reaction mixture and the solvent are conventionally separated off by means of an arrangement of distillation columns which successively fractionate the fractions according to their number of carbon atoms. As an alternative, the work-up by distillation can be carried out using side offtake columns. The isolation by distillation is effected directly from the first reaction mixture or from a stream based thereon. The latter can be a mixture of a further stream occurring within the process and the first reaction mixture or be a remainder of the first reaction mixture after a fraction, cf. $C_2$, has been separated off therefrom.

It will not be possible to react the hexene completely in the second synthesis. The reason is that the hexene is utilised not only as starting material but also partly as solvent for ethene in order to keep the latter in the liquid phase. There is therefore an excess of hexene in the second synthesis, which leads to unreacted hexene being present in the second reaction mixture. According to the inventive aspect of the circulation of solvent with hexene, it should be separated off from the second reaction mixture and at least partly recirculated to the second synthesis. The separation of the hexene and of the solvent from the second reaction mixture can be carried out by blending the latter with the first reaction mixture, so that the separation of the fraction composed of hexene and solvent from the second reaction mixture occurs together with the separation of hexene and solvent from the first reaction mixture, as a result of which the synergistic effect of the saving of columns is again achieved.

On the one hand, it is important that the ethene is very largely present as a solution in the solvent since a gas phase composed of undissolved ethene decreases the process intensity in the two heterogeneously catalysed syntheses: Ethylene gas bubbles in the liquid solvent increase the volume of the feed mixture, which in turn makes a larger catalyst and reactor volume necessary. Furthermore, the flow dynamics in the catalyst bed are made more difficult to control by undissolved ethene. In addition, direct contact of the undiluted gaseous ethene with the catalyst can lead to increased occurrence of strongly exothermic polymerisation; the catalyst should therefore always be wetted with liquid if possible.

On the other hand, a high linear velocity in combination with a bubbling phase with a sufficiently high liquid loading (pulse flow regime) can ensure that the liquid phase becomes saturated again more quickly by operation in the region of turbulent liquid flow, as is known from experience with hydrogenations (e.g. EP 0319208A1).

For this reason, an alternative possibility is to carry out the reaction in the bubbling phase with sufficiently high liquid loading, that is to say with part of the ethene in the gas phase at the reactor inlet, i.e. as ethene gas bubbles in the liquid $C_5$-$C_7$ solvent, which serve for rapid subsequent saturation of the liquid phase in the further course of the reaction.

The first target product of the process of the invention is 1-butene. It has the best reactivity and linearity among all the butenes and is therefore a sought-after synthetic building block which should be isolated in isomerically pure form if possible. This can be effected by means of a distillation in which 1-butene present in the butene separated off is isolated by separating it by distillation from 2-butene present in the butene separated off. The isolation of the isomers by distillation is economical because of the boiling point position. Here, 1-butene goes over at the top while cis-2-butene and trans-2-butene remain in the bottoms.

This separation is driven by 2-butene being continuously taken off from the bottom of the distillation column. These two less attractive 2-butenes obtained there can be increased in value by means of an isomerisation in which 2-butene present in the butene which has been separated off is at least partially isomerised to 1-butene; to give an isomerisation mixture which is recirculated to the distillation in which 1-butene is isolated. In this context, isomerisation means that the thermodynamic equilibrium in a mixture of 1-butene, cis-2-butene and trans-2-butene is shifted in favour of 1-butene. The isomerisation of 2-butene to 1-butene is described, for example, in EP0718036A1. The isomerisation is thus able to increase the yield of 1-butene. In addition, it allows an energy saving since the distillation at the top of which 1-butene is obtained does not have to be carried out under such severe conditions because 1-butene is allowed to remain in the bottoms. Furthermore, the isomerisation does not have to be made so large when 2-butene is discharged from the process at the bottom of the distillation in which 1-butene is isolated.

A second possible way of utilising 2-butene from the bottom of the column for separating off 1-butene is to carry out an oxidative dehydrogenation to butadiene. The reaction to form butadiene does not have to proceed to completion. Butadiene, more precisely 1,3-butadiene, is used in large quantities for producing synthetic rubber and can therefore be marketed readily. Before the oxidative dehydrogenation, it is possible to carry out an isomerisation of 2-butene to 1-butene. The technology required for preparing butadiene by oxidative dehydrogenation of n-butene by means of the above isomerisation is comprehensively described in the German patent application 102013226370.8 which is still unpublished at the time of filing of the present application.

Finally, the 2-butene from the bottom of the column for separating off 1-butene can be at least partly converted into octene to give a third reaction mixture which can be worked up together with the first reaction mixture. The reaction itself is an oligomerisation which can, but does not have to, be carried out according to the Octol® process. However, carrying out the reaction according to the Octol® process is preferred since this gives high-quality dibutene. The work-up of the oligomerisation mixture obtained in this way from the third synthesis is carried out together with the oligomerisation mixture from the $C_2$ oligomerisation, since columns can be saved in this way.

The first synthesis should be carried out at a temperature in the range from 20° C. to 150° C. and a pressure in the range from $1*10^5$ Pa to $50*10^5$ Pa, with the process conditions being selected so that the solvent is present in liquid form.

The proportion of ethene in the first feed mixture is preferably in the range from 1% by weight to 50% by weight. In the interests of process intensity, the proportion of ethene in the first feed mixture and the reaction conditions of the first synthesis should be matched in such a way that the solvent is present in the liquid phase in the first synthesis.

The ethene can be completely dissolved in the solvent, so that the reaction takes place entirely in the liquid phase. The ethene concentration in the solvent and the reaction conditions should accordingly be selected so that the ethene always remains in solution.

As an alternative, the reaction can also be carried out in the bubbling phase. This means that although the solvent is present in liquid form with ethene dissolved therein, part of the ethene is also present in the gas phase and a gas/liquid reaction is thus carried out. The ethene concentration in the solvent and the reaction conditions should accordingly be selected so that the ethene is partly dissolved and partly present in the gas phase.

The first synthesis is preferably operated with a conversion in the range from 50% to 100%, a selectivity to $C_4$ of from 50% to 95% and a selectivity to $C_8$ of from 0% to 20%.

In the second synthesis, too, the reaction conditions should be selected so that the hexene and any further solvent are present in the liquid phase. The preferred proportion of ethene in the second feed mixture is in the range from 0.1% by weight to 30% by weight; the second synthesis should be carried out at a temperature in the range from 20° C. to 150° C. and a pressure in the range from $1*10^5$ Pa and $50*10^5$ Pa. The second synthesis is preferably operated at a conversion in the range from 90% to 100%, a selectivity to $C_4$ of from 0% to 70% and a selectivity to $C_8$ of from 20 to 80%.

In principle, the second feed mixture should contain a higher proportion by weight of hexene than of ethene in order to provide an excess of hexene.

The proportion of ethene in the second feed mixture is preferably less than 30% by weight, very particularly preferably less than 20% by weight. This is because an excess of $C_6$ over $C_2$ favours the reaction of $C_6$ with $C_2$ relative to $C_2$ with $C_2$.

In order to be able to carry out both reactions in the liquid phase or in the bubbling phase, both reactions are carried out in a solvent which is liquid under the reaction conditions.

The solvent is preferably at least one hydrocarbon having five, six or seven carbon atoms. Hydrocarbons having more than seven carbon atoms cannot be used since these remain in the bottoms from the column and have to be separated off separately from the desired product octene. Hydrocarbons having fewer than five carbon atoms are likewise less suitable as solvents since these go over at the top in the distillation and therefore mean a greater energy consumption. A solvent which has a boiling point between that of the first target product 1-butene and that of the second target product 1-octene should therefore be used. These are the hydrocarbons having five, six and seven carbon atoms. It is also possible to use mixtures of different hydrocarbons having the same number or different numbers of carbon atoms. This generally leads to the mixture used as solvent not having a singular boiling point but instead a boiling range which, as is desirable, lies between the boiling point of the two target products. The comparison of the boiling points is a comparison of the boiling temperatures at the same pressure.

Preference is given to using the appropriate C5-C7-alkanes as solvent. This is because alkanes are, owing to their saturated compounds, far less reactive than alkenes and are therefore inert in both reactions. Since they do not change in the reaction, it is simpler in process engineering terms to maintain the circulation through the two reactions. For this reason, pentane, hexane or heptane, either individually or as a mixture, is therefore used as solvent. It is also possible to use the cyclic alkanes cyclopentane, cyclohexane and cycloheptane.

Accordingly, the two feed mixtures are in each case provided so that they contain at least one alkane having five or six or seven carbon atoms.

Apart from the $C_5$-, $C_6$- and $C_7$-alkanes, the $C_6$-olefin hexene can be used as solvent since it has the desired boiling point position. If the total amount of hexene formed over the two reactions is the same as that which is reacted, the circuit is stable. In the overall balance, hexene is pseudoinert, although it may very well be reacted in the individual balances of the respective reactions. If the hexene balance is not equalized, hexene can be added from the outside or can be discharged to the outside. In such a case, it is advisable to provide a buffer storage for hexene into which any overproduction of hexene is discharged and from which hexene is taken in the case of underproduction.

Hexene alone or admixed with pentane or hexane or heptane or mixtures of these $C_5$-$C_7$-alkanes can thus be used as solvent. The use of hexene alone as solvent represents a special case of the present invention, in which a reactive solvent is used. The $C_5$- and $C_7$-olefins are, on the other hand, not suitable as solvents since they are not inert in the reactions and instead form undesirable by-products which once again have to be separated off in a complicated manner.

A mixture of hexane and hexene has been found to be an optimal solvent: This is because less hexene is consumed in the first reaction in the presence of hexane, so that the solvent circuit can be maintained. In excessively high concentrations, pure hexene is so reactive that it reacts to an increasing extent with itself to form $C_{8+}$ and for this reason more $C_6$ is consumed than has been initially charged. The precise ratio of hexane to hexene has to be determined with a view to the reaction of hexene and ethene to form octene (in the second reaction) and depends essentially on the catalyst used.

A particular advantage of the process presented here compared to the industrially operated production of octene is that a heterogeneous catalyst which remains in the reactor and not in the product is used. The catalyst is thus a solid which is preferably installed as a fixed bed in the respective reactor. The same catalyst or different catalysts can be provided for carrying out the first synthesis and the second synthesis. First and second catalysts can thus be identical, but do not have to be. However, the two catalysts should be arranged physically separately from one another, best in different reaction vessels but at least as different beds in the same reaction vessel.

A specific, suitable first and/or second heterogeneous catalyst is a solid which contains at least two components, where the first component comprises at least one element which is selected from among Ni, Cr, Fe, Ti and is present in metallic and/or oxidic and/or hydridic form and the second component comprises at least one metal oxide selected from among $Al_2O_3$, $SiO_2$, $TiO_2$, $ZrO_2$.

Particular preference is given to using a catalyst which comprises nickel as first component and silica as second component. Such a catalyst is disclosed in U.S. Pat. No. 2,581,228.

Figure 2:
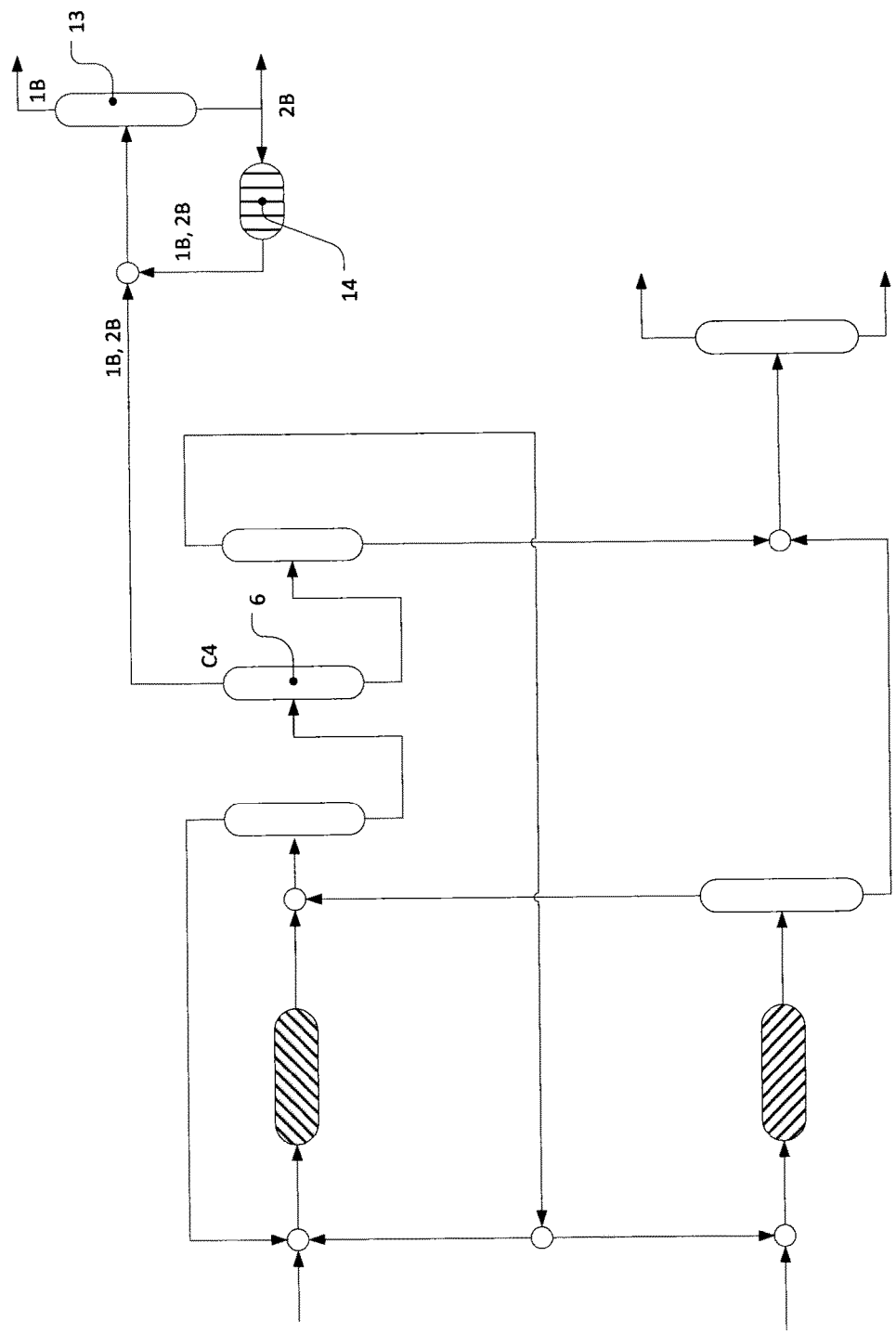
FIG. 2 shows the same as FIG. 1, additionally with isomerization.
Figure 3:
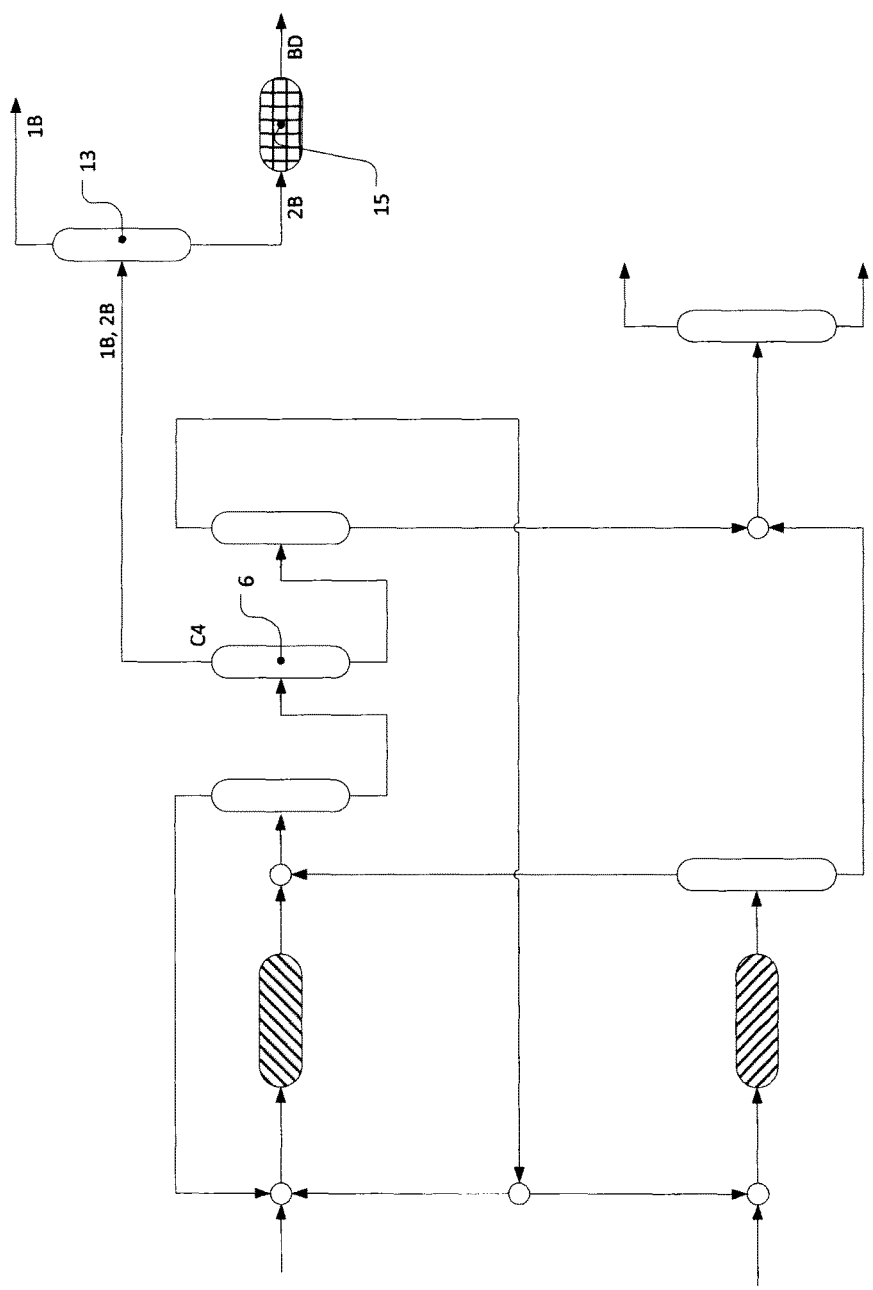
FIG. 3 shows the same as FIG. 1, additionally with oxidative dehydrogenation.
Figure 4:
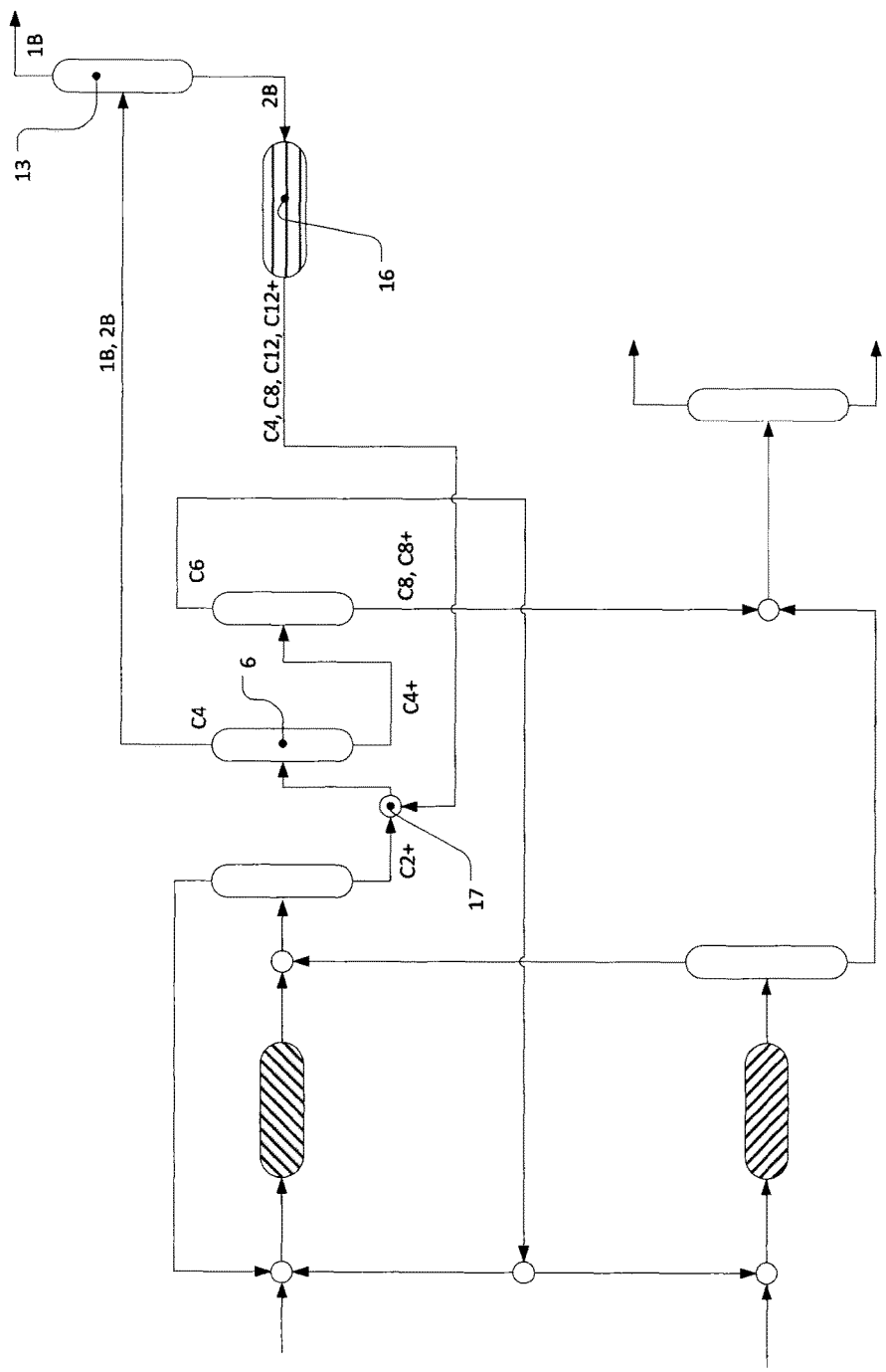
FIG. 4 shows the same as FIG. 1, additionally with $C_4$ oligomerisation.

Possible examples of the layout of a coupled process which encompasses both $C_2$ oligomerisation and the reaction of ethylene with hexene in the presence of hexane as solvent will now be illustrated with the aid of the figures. The figures show:

FIG. 1: Basic concept of the process of the invention;
FIG. 2: Variant with isomerisation;
FIG. 3: Variant with oxidative dehydrogenation;
FIG. 4: Variant with $C_4$ oligomerisation.

All figures are schematic and merely show the essential constituents of a corresponding plant for carrying out the process of the invention.

FIG. 1 shows the basic principle. There are two syntheses 1, 2 which are operated in parallel and are carried out in physically separate reactors. The first synthesis 1 is an oligomerisation of ethene. This serves primarily to prepare butene. The second synthesis 2 serves for preparing octene from ethene and hexene.

The ethene C2 required for the two syntheses 1, 2 originates from one or more sources which are not shown here. The purity of the ethene C2 which flows in as a liquid or gas is more than 99.9%. As accompanying materials, it is possible for less than 10 ppm of oxygen, less than 5 ppm of carbon monoxide, less than 10 ppm of carbon dioxide and less than 1000 ppm of other hydrocarbons to occur. A higher purity is not necessary since the most frequent impurities are inert alkanes such as ethane or methane which do not interfere in the reaction itself and, in the case of relatively high proportions, merely change the boiling and pressure ranges slightly.

A mixer 3, 4 is assigned to each synthesis 1, 2. The first mixer 3 serves to provide a first feed mixture C2, C6, SOLV for the first synthesis 1. The first feed mixture is a liquid hexene/hexane mixture C6, SOLV with ethene C2 completely dissolved therein. The hexene/hexane mixture C6, SOLV comes from a C6 recycle stream, while the ethene C2 comes partly from the source and partly from an ethene recycle stream. The composition of the first feed mixture is set in the first mixer 3 so that it is liquid under the reaction conditions in the first synthesis and the ethene is completely dissolved in the hexane/hexene mixture.

In the first synthesis 1, the ethene is oligomerised in the presence of a first heterogeneous catalyst and in the presence of hexene and hexane. This forms butenes C4, hexenes C6, octenes C8 and higher olefins C8+. Part of the ethene C2 is not reacted. Whether hexene C6 is reacted is unknown. This is possible but cannot be established since fresh hexene is simultaneously formed by trimerisation of ethene. However, the process conditions are set so that hexene increases in the output in the mass balance of the first synthesis. Thus, more hexene is formed in the first synthesis 1 than is reacted. Overall, the first reaction output comprises C2, C4, C6, C8, C8+, SOLV, unreacted ethene, selectively formed butene, old and freshly formed hexene, octene formed and higher olefins formed. Since the hexane SOLV is inert in the reaction, this is also present in the first reaction mixture.

The first reaction mixture C2, C4, C6, C8, C8+, SOLV is worked up by distillation with the aid of a series of three columns 5, 6, 7. The first column 5 separates off ethene C2 at the top, so that the olefins having more than two carbon atoms C2+ remain in the bottoms. The ethene C2 which has been taken off at the top of the first column 5 is recirculated as ethene runback to the first mixer 3.

The second column 6 then separates off the butenes C4 originating from the first reaction mixture as a low boiler fraction at the top. The low boiler fraction contains essentially 1-butene 1B and cis/trans-2-butene 2B. The olefins having more than four carbon atoms C4+ are conveyed from the bottom of the second column 6 into the third column 7. There, hexene C6 and hexane SOLV are separated off as intermediate boiler fraction at the top, so that octene C8 and the higher olefins C8+ remain in the bottoms.

The intermediate boiler fraction which is separated off in the third column 7 and is composed of hexene C6 and solvent hexane SOLV is recycled to a divider 8 which divides the intermediate boiler runback between the first mixer 3 and the second mixer 4.

In the second mixer 4, fresh ethene C2 is dissolved in the recycled intermediate boiler composed of hexene C6 and hexane SOLV, so that a second feed mixture C2, C6, SOLV is formed. Ethene runback from the first column 5 or from an ethene column arranged downstream of the second synthesis 2 can also be added to the fresh ethene, although this is not the case in the embodiment shown in FIG. 1.

The composition of the second feed mixture C2, C6 is set in the second mixer 4 so that it is liquid under the reaction conditions in the second synthesis 2 and the ethene is completely dissolved in the hexene/hexane mixture.

In the second synthesis, ethene C2 and hexene C6 are then reacted in the presence of a heterogeneous catalyst to form octene C8. The reaction is optimised in the direction of octene by the presence of the inert hexane as solvent SOLV. Nevertheless, secondary reactions still take place in the second synthesis 2 since butenes C4 and higher olefins C8+ are also formed there. In addition, it is possible to conceive that octene is formed by tetramerisation of ethene in the second synthesis.

The second synthesis 2 is operated so that the amount of hexene formed in the first synthesis 1 is consumed again in the second synthesis 2. A buildup of hexene in the plant is thus avoided. If the amount of hexene which can be converted into octene in the second synthesis is less than the amount formed in the first synthesis, hexene has to be discharged from the system so that the plant does not fill up with hexene. The discharge can, for example, be effected at the top of the third column 7. However, this is not desirable and is therefore also not shown in FIG. 1.

Conversion of more hexene into C8 and C8+ than is freshly formed, which would lead to problems in maintaining the solvent circuit, can be avoided by addition of an inert solvent such as hexane. Unlike hexene, the inert solvent is not formed in the process but instead has to be introduced from the outside before start-up. If it ages, i.e. does not behave in an ideally inert manner, it has to be replaced from time to time.

The second reaction mixture C2, C4, C6, C8, C8+, SOLV taken off from the second synthesis comprises the same olefins as the first reaction mixture but in a different composition. The inert solvent hexane SOLV is likewise present. The second synthesis 2 forms predominantly octene, so that the $C_8$ content of the second reaction mixture is higher than that in the first reaction mixture. The latter in turn has a higher $C_4$ content.

Owing to the qualitatively similar composition, the second reaction mixture can be worked up together with the first reaction mixture. It can be fed directly together with the first reaction mixture into the series of columns 5, 6, 7.

However, it makes sense to firstly fractionate the second reaction mixture by distillation to give a fraction composed of low and intermediate boilers C2, C4, C6 and a high boiler fraction C8, C8+, for which purpose a fourth column 9 is provided. Since the second synthesis 2 produces more octene and higher olefins, the high boiler fraction C8, C8+ is significantly larger than the low and intermediate boiler fraction C2, C4, C6. For this reason, the fourth column 9 can be operated with a comparatively low energy consumption. Since the high boilers C8, C8+ from the second synthesis do not have to be passed through the series of columns 5, 6,7, the three columns 5, 6, 7 also do not have to be made so large.

The combining of the low and intermediate boiler fraction C2, C4, C6 originating from the fourth column with the first reaction mixture C2, C4, C6, C8, C8+, SOLV occurs in a third mixer 10 which is arranged upstream of the first column 5.

The high boiler fraction C8, C8+ from the fourth column 9 corresponds qualitatively to the bottoms from the third column 7. For this reason, the two streams can be combined in a fourth mixer 11 and fractionated together by distillation in a fifth column 12. Octene C8 is taken off as second target product from the top of the fifth column, while the higher olefins C8+ remain in the bottoms and are separately utilised as unavoidable by-product.

Now back to the first target product butene C4 which is obtained as low boiler fraction at the top of the second column 6.

The butene C4 obtained there is not isomerically pure, but instead is an isomer mixture 1B, 2B composed of 1-butene and cis-2-butene and trans-2-butene. The overhead product from the second column is thus linear n-butene. Happily, it does not contain any branched isobutene since this is not formed in the first synthesis. A complicated removal of isobutene, which is necessary in the isolation of n-butene from $C_4$ streams, can therefore be dispensed with in this process based on ethene.

The economics of the process can be improved by the butene mixture C4 from the top of the second column 6 being worked up further in the direction of 1-butene. FIGS. 2, 3 and 4 each show a proposal for this.

A feature common to these three variants is a sixth column 13 which is provided for separation of 1-butene 1B and 2-butene 2B by distillation. 1-Butene 1B has a lower boiling point than cis-2-butene and trans-2-butene and can therefore be taken off in high purity from the top of the sixth column 13.

There are then three possibilities for use of the 2-butene 2B at the bottom of the sixth column 13:

In the first variant as shown in FIG. 2, the 2-butene is subjected to an isomerisation 14 which partly converts the 2-butene into 1-butene. The isomerisation 14 again results in an isomer mixture 1B, 2B of 1-butene and 2-butene which is mixed with the overhead product from the second column 6 and is again fed into the sixth column 13. For thermodynamic reasons, the isomerisation of the 2-butene can never be complete. It is therefore necessary for 2-butene 2B to be continually discharged from the bottom of the sixth column 13.

As an alternative, the 2-butene 2B from the bottom of the sixth column 13 can be subjected to an oxidative dehydrogenation 15. This is shown in FIG. 3. In the oxidative dehydrogenation 15, the 2-butene is converted into 1,3-butadiene BD, which is a chemical having greater value added than 2-butene. The oxidative dehydrogenation can also be preceded by an isomerisation of 2-butene to 1-butene since 1-butene reacts more rapidly to form butadiene than does 2-butene. The optional isomerisation is not shown in FIG. 3.

Finally, as shown in FIG. 4, the 2-butene 2B from the bottom of the sixth column 13 can be fed to a third synthesis 16 in which it is at least partly oligomerised to octene. This preferably occurs in an Octol® process which forms not only dibutene but also olefins having twelve and more carbon atoms C12, C12+. The third reaction mixture C4, C8, C12, C12+ obtained in this way is mixed with the bottoms C2+ from the first column 5 in a sixth mixer 17 and fed to the second column 6. The work-up of the third reaction mixture thus occurs together with the first reaction mixture and the second reaction mixture.

In all of the three variants shown in FIGS. 2, 3 and 4 for working up the butene-containing low boiler fraction C4, the latter is not burdened with the solvent SOLV since this has a higher boiling point than the butenes and therefore remains in the bottoms from the column 6, from the top of which the butenes are separated off as low boiler fraction C4. The energy consumption of the column 6 is therefore reduced and, secondly, the C4 work-up is not burdened with inert material, so that the apparatuses can be made smaller.

Having generally described this invention, a further understanding can be obtained by reference to certain specific examples which are provided herein for purposes of illustration only, and are not intended to be limiting unless otherwise specified.

The invention will now be explained in more detail by reference to examples.

EXAMPLES

Example 1

Oligomerisation of Ethene in n-Hexane with Focus on 1-Butene (First Reaction)

15.5 g of a heterogeneous catalyst based on nickel and silica-alumina (cf. U.S. Pat. No. 2,581,228) were introduced into a tube reactor which had a length of 1 m and an internal diameter of 6 mm and whose temperature was controlled from the outside by means of oil. A mixture of 17% by mass of ethene, 77% by mass of n-hexane and 6% by mass of the internal standard n-heptane was subsequently passed through at a total flow rate of 100 g/h and a temperature of 70° C. (WHSV=6.4/h). The pressure was kept constant at 30 bar. After a time of 60 hours, a state in which the conversion no longer changed had been reached. The results are summarised in Table 1. For further analysis, the product fraction was injected into a hydrogenating gas chromatograph. The compositions of the hydrogenated C8 fraction are likewise summarised in Table 1.

Example 2

Oligomerisation of Ethene in n-Hexene with Focus on 1-Butene (First Reaction)

In a manner analogous to Example 1, 15.5 g of the same catalyst were introduced into a tube reactor which had a length of 1 m and an internal diameter of 6 mm and whose temperature was controlled from the outside by means of oil. A mixture of 20% by mass of ethene, 73% by mass of n-hexene and 7% by mass of the internal standard n-heptane was subsequently passed through at a total flow rate of 105 g/h and a temperature of 70° C. (WHSV=6.8/h). The pressure was kept constant at 30 bar. After a time of 73 hours, a state in which the conversion no longer changed had been reached. The results and the composition of the hydrogenated C8 fraction are summarised in Table 1.

Example 3

Oligomerisation of Ethene in an n-Hexene/n-Hexane Mixture with Focus on 1-Butene (First Reaction)

In a manner analogous to Example 1, 4.1 g of the same catalyst were introduced into a tube reactor which had a length of 1 m and an internal diameter of 6 mm and whose temperature was controlled from the outside by means of oil. A mixture of 17% by mass of ethene, 45% by mass of n-hexene and 38% by mass of n-hexane was subsequently passed through at a total flow rate of 100 g/h and a temperature of 70° C. (WHSV=24.2/h). The pressure was kept constant at 30 bar. After a time of 72 h, a state in which the conversion no longer changed had been reached. The results and the compositions of the hydrogenated $C_8$ fraction are summarised in Table 1.

Example 4

Oligomerisation of Ethene in an n-Hexene/n-Hexane Mixture with Focus on Octene (Second Reaction)

In a manner analogous to Example 3, a mixture of 5% by mass of ethene, 53% by mass of n-hexene, 30% by mass of n-hexane and 12% by mass of the internal standard n-heptane was passed at a total flow rate of 100 g/h and a temperature of 70° C. (WHSV=6.4/h) over 15.5 g of a catalyst. The pressure was kept constant at 30 bar. After a time of 72 hours, a state in which the conversion no longer changed had been reached. The results and the compositions of the hydrogenated C8 fraction are summarised in Table 1.

TABLE 1

Results of Examples 1 to 4

| Example | Conversion | C4 | C6 | C8 | C8+ | 1-butene | 2-butene | Sel. nO | Sel. MH | Sel. DMH |
|---|---|---|---|---|---|---|---|---|---|---|
| 1 | 99% | 68% | 21% | 8% | 3% | 19% | 81% | 41% | 51% | 7%[a] |
| 2 | 98% | 58% | 8%[e] | 25% | 9% | 45% | 55% | 30% | 68% | 2%[b] |
| 3 | 92% | 71% | −2%[e] | 23% | 8% | 33% | 67% | 30% | 68% | 2%[c] |
| 4 | 99% | 51% | 15%[e] | 29% | 7% | 31% | 69% | 31% | 66% | 1%[d] |

In Table 1, the footnotes have the following meanings:
a-d) The iso index of the C8 mixture is 0.65 for a), 0.72 for b) and c) and 0.68 for d); e) C6 results from freshly formed hexene minus the hexene consumed.

The abbreviations have the following meanings: Sel. is selectivity, nO is n-octene, MH is methylheptene and DMH is dimethylhexene.

CONCLUSION

The reaction in pure n-hexane (Example 1) results in a high C4 selectivity and a low C8 selectivity. At the same time, 1-butene is more strongly isomerised and reacted further under these conditions, so that the 1-butene selectivity is comparatively low. In addition, it is conspicuous that a quite large amount of C6 is formed. This can, as a result of reaction conditions in pure n-hexene (Example 2), be mostly utilised by further reaction to form C8, although at the same time the C4 selectivity drops and the proportion of C8+ formed by oligomerisation of C6 increases.

The reactivity of the n-hexene can be reduced by dilution with n-hexane, so that the consumption of C6 can be controlled in a more targeted manner and the circuit can thus be maintained more readily. The formation of C8 and C8+ is somewhat lower here. In addition, the C4 selectivity and the 1-butene selectivity can be increased by reducing the residence time (WHSV 24 instead of 6) (Example 3). At the same hexene/hexane ratios, a lower ethene content (Example 4 compared to Example 3) leads to decreased formation of C4 (51% vs. 71%) and increased formation of C8 (29% vs. 23%), all in the sense of synthesis 2.

In all cases, the C8 mixture has a significantly more favourable iso index than can be achieved at present by the butene oligomerisation route (0.65-0.72 vs. >0.9).

Overall, somewhat more hexene is consumed than is freshly formed in the case of dilution of n-hexene with n-hexane under these reaction conditions in synthesis 1 (Example 3), while in synthesis 2 (Example 4) more hexene is formed than is consumed; in the total balance, a certain purge C6 stream therefore arises in this case and has to be removed from the circuit. In synthesis 1 (Example 3) 1-butene is preferentially formed, as desired, while comparatively more C8 is produced in synthesis 2 (Example 4).

Finally, the important aspects and advantages of the invention will be summarised:

The heterogeneously catalysed process presented here serves for the combined preparation of butene and octene from ethene. It encompasses two reactions carried out simultaneously, namely a first synthesis primarily of $C_2$ to $C_4$ and a second synthesis of $C_2$ and $C_6$ to $C_8$. The two reactions are operated physically separately from one another. Both syntheses are carried out in the presence of an inert solvent whose boiling point lies between those of the butenes and of the octenes. In the first synthesis, hexene and octene are also formed in addition to the first target product butene. The hexene formed in the first synthesis in the course of the $C_2$ trimerisation is used as starting material for the second synthesis. There, it is reacted with ethene to form octene, the second target product. The actually undesirable by-product from the first synthesis hexene is thus used further for forming octene. Finally, the solvent is continually circulated. This makes it possible to carry out both syntheses in the liquid phase and to control the selectivity of the reactions. Since the boiling point of the solvent corresponds essentially to that of the by-product hexene, the by-product can be separated off together with the solvent as intermediate boiler from the first reaction mixture and be transferred to the second reaction.

European patent application EP15151621 filed Jan. 19, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for the combined preparation of a butene and an octene from ethene, said process comprising:
   a) providing a solvent having a boiling point or boiling range above the boiling points of the butenes and below the boiling points of the octenes and wherein the solvent is a first inert solvent or is hexene admixed with said first inert solvent;
   b) providing a first feed mixture containing at least the solvent and ethene dissolved therein;
   c) providing a second feed mixture containing at least hexene, optionally a second inert solvent having a boiling point or boiling range above the boiling points of the butenes and below the boiling points of the octenes, and ethene dissolved in the hexene and said second inert solvent, when present, said second feed mixture containing a higher proportion by weight of hexene than of ethene;
   d) transferring the first feed mixture into a first synthesis and the second feed mixture into a second synthesis, wherein the first and second syntheses are physically separated from one another;
   e) oligomerising at least a part of the ethene present in the first feed mixture in the presence of a first heterogeneous catalyst, thereby producing a first reaction mixture comprising at least butene, hexene, and said first inert solvent;
   f) separating a butene-containing low boiler fraction from the first reaction mixture or from a stream based on the first reaction mixture;
   g) separating an intermediate boiler fraction containing hexene and said first inert solvent, from the first reaction mixture or from a stream based on the first reaction mixture;
   h) using at least part of the intermediate boiler fraction in the course of providing the second feed mixture; and
   i) reacting at least a part of the ethene present in the second feed mixture with at least part of the hexene present in the second feed mixture in the presence of a second heterogeneous catalyst and said second inert solvent, when present, in the second synthesis, thereby producing a second reaction mixture comprising at least octene with an iso index of less than 1.1, and said second inert solvent, when present:
   wherein the first heterogeneous catalyst and the second heterogeneous catalyst comprises at least a first component and a second component,
   wherein a first component comprises at least one element selected from the group consisting of Ni, Cr, Fe, and Ti, which is present in a metallic and/or oxidic and/or hydridic form, and
   wherein a second component comprises at least one metal oxide selected from the group consisting of $Al_2O_3$, $SiO_2$, $TiO_2$, and $ZrO_2$; and
   wherein said first synthesis and said second synthesis are carried out simultaneously.

2. The process according to claim 1, wherein ethene present in the first reaction mixture and/or in the second reaction mixture is separated off and used for providing the first and/or second feed mixture.

3. The process according to claim 1, wherein the second reaction mixture further comprises butene, and the butene present in the second reaction mixture is worked up together with the butene present in the first reaction mixture.

4. The process according to claim 1, wherein the second reaction mixture further comprises hexene, and the hexene present in the second reaction mixture is separated off and at least partly recirculated to the second synthesis.

5. The process according to claim 1, wherein said first inert solvent and/or said second inert solvent, when present, is a hydrocarbon having five or six or seven carbon atoms or a mixture of a plurality of such hydrocarbons.

6. The process according to claim 1, wherein the proportion of ethene in the first feed mixture is from 1 to 50% by weight and wherein the first synthesis is carried out at a temperature of from 20° C. to 150° C. and at a pressure of from $1*10^5$ Pa to $50*10^5$ Pa, wherein the proportion of ethene in the first feed mixture and the reaction conditions of the first synthesis are selected so that the solvent is present in the liquid phase.

7. The process according to claim 6, wherein the proportion of ethene in the first feed mixture and the reaction conditions of the first synthesis are selected so that the ethene is completely dissolved in the solvent present in the liquid phase in the first synthesis.

8. The process according to claim 6, wherein the proportion of ethene in the first feed mixture and the reaction conditions of the first synthesis are selected so that the ethene is partly present in a gas phase and is partly dissolved in the solvent present in the liquid phase in the first synthesis.

9. The process according to claim 1, wherein the proportion of ethene in the second feed mixture is from 0.1 to 30% by weight and wherein the second synthesis is carried out at a temperature of from 20 to 150° C. and at a pressure of from $1*10^5$ Pa to $50*10^5$ Pa, wherein the proportion of ethene in the second feed mixture and the reaction conditions of the second synthesis are selected so that the hexene and said second inert solvent, when present, are present in the liquid phase and the ethene is completely dissolved therein.

10. The process according to claim 1, wherein the proportion of ethene in the second feed mixture is less than 30% by weight.

11. The process according to claim 1, wherein said first inert solvent and/or said second inert solvent, when present, is n-hexane.

12. The process according to claim 1, wherein the proportion of ethene in the second feed mixture is less than 20% by weight.

13. The process according to claim 1, wherein said first inert solvent and/or said second inert solvent, when present, is pentane or hexane or heptane or is a mixture of pentane, hexane, and heptane.

* * * * *